US011540813B2

(12) United States Patent
Nieminen et al.

(10) Patent No.: US 11,540,813 B2
(45) Date of Patent: Jan. 3, 2023

(54) HANDHELD ULTRASOUND IMAGING SYSTEMS AND METHODS FOR COOLING TRANSDUCERS AND ELECTRONICS IN THE PROBE HOUSING VIA AIR CIRCULATION THROUGH THE HOUSING

(71) Applicant: FUJIFILM Sonosite, Inc., Bothell, WA (US)

(72) Inventors: Greg Nieminen, Bothell, WA (US); Todd Willsie, Seattle, WA (US); Evan McCormack, Kenmore, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 95 days.

(21) Appl. No.: 14/301,299

(22) Filed: Jun. 10, 2014

(65) Prior Publication Data

US 2015/0351727 A1 Dec. 10, 2015

(51) Int. Cl.
*A61B 8/00* (2006.01)
*A61B 8/08* (2006.01)

(52) U.S. Cl.
CPC .......... *A61B 8/546* (2013.01); *A61B 8/4455* (2013.01); *A61B 8/08* (2013.01); *A61B 8/4483* (2013.01); *Y10T 29/49007* (2015.01)

(58) Field of Classification Search
CPC ......... A61B 8/00; A61B 8/546; A61B 8/4455; A61B 8/08; A61B 8/4483; Y10T 29/49007
USPC ........................................................ 600/459
See application file for complete search history.

(56) References Cited

U.S. PATENT DOCUMENTS

| | | | | |
|---|---|---|---|---|
| 4,973,247 A | * | 11/1990 | Varnes | A61C 1/05 |
| | | | | 433/82 |
| 5,353,868 A | * | 10/1994 | Abbott | B21D 53/045 |
| | | | | 165/147 |
| 5,494,038 A | | 2/1996 | Wang et al. | |
| 5,551,945 A | * | 9/1996 | Yabe | A61B 1/00142 |
| | | | | 600/121 |
| 5,560,362 A | * | 10/1996 | Sliwa, Jr. | A61B 8/546 |
| | | | | 600/439 |

(Continued)

FOREIGN PATENT DOCUMENTS

| | | |
|---|---|---|
| CN | 1765329 | 5/2006 |
| JP | 2008194278 A | 8/2008 |

(Continued)

OTHER PUBLICATIONS

International Searching Authority, International Search Report and Written Opinion, PCT Patent Application PCT/US2015/034980, dated Sep. 16, 2015, 12 pages.

(Continued)

*Primary Examiner* — Serkan Akar
(74) *Attorney, Agent, or Firm* — Womble Bond Dickinson (US) LLP

(57) ABSTRACT

Systems and methods of transmitting heat away from an ultrasound probe are disclosed within. In one embodiment, a handheld ultrasound probe includes a transducer, electronics configured to drive the transducer, and a housing surrounding the transducer assembly and the electronics. A slot extending from a first side of the housing to a second side of the housing and can allow air to pass adjacent transducer and the electronics. The slot can be sized to inhibit accessibility of an operator's finger to an inner surface of slot.

11 Claims, 4 Drawing Sheets

(56) References Cited

U.S. PATENT DOCUMENTS

| | | | | |
|---|---|---|---|---|
| 5,961,465 | A * | 10/1999 | Kelly, Jr. | A61B 8/546 600/459 |
| 6,142,945 | A * | 11/2000 | Sakamoto | A61B 1/018 600/459 |
| 6,142,947 | A | 11/2000 | Tran et al. | |
| 8,932,279 | B2 * | 1/2015 | Stringham | A61B 18/082 606/29 |
| 2005/0038340 | A1 * | 2/2005 | Vaezy | A61B 8/06 600/439 |
| 2005/0180894 | A1 * | 8/2005 | Petroff | B01L 3/502715 422/400 |
| 2005/0273127 | A1 | 12/2005 | Novak et al. | |
| 2006/0100513 | A1 * | 5/2006 | Hashimoto | A61B 8/00 600/437 |
| 2008/0146924 | A1 * | 6/2008 | Smith | G01S 7/52017 600/437 |
| 2009/0071625 | A1 | 3/2009 | Lyon et al. | |
| 2010/0109480 | A1 | 5/2010 | Forslund et al. | |
| 2010/0211136 | A1 * | 8/2010 | De Taboada | A61N 5/0617 607/88 |
| 2010/0228130 | A1 | 9/2010 | Chiang et al. | |
| 2010/0331702 | A1 * | 12/2010 | Hongou | A61B 8/14 600/459 |
| 2012/0143060 | A1 | 6/2012 | Weekamp et al. | |
| 2012/0223618 | A1 | 9/2012 | Clark et al. | |
| 2013/0115506 | A1 | 5/2013 | Wayne et al. | |
| 2013/0286593 | A1 | 10/2013 | Cho et al. | |
| 2013/0338508 | A1 * | 12/2013 | Nakamura | A61B 8/4444 600/459 |
| 2014/0058270 | A1 * | 2/2014 | Davidsen | G01S 15/8925 600/472 |
| 2014/0371946 | A1 * | 12/2014 | Kwak | H01M 10/625 700/300 |
| 2015/0099978 | A1 * | 4/2015 | Davidsen | A61B 8/4483 600/459 |
| 2015/0282878 | A1 * | 10/2015 | Kindermann | A61B 18/18 606/9 |

FOREIGN PATENT DOCUMENTS

| | | | | |
|---|---|---|---|---|
| JP | 2008284003 | A | 11/2008 | |
| JP | 2010088610 | A | 4/2010 | |
| WO | 2014064608 | | 5/2014 | |
| WO | 2015029637 | * | 5/2014 | A61B 8/546 |

OTHER PUBLICATIONS

European Patent Office, Extended European Search Report, EP Patent Application 15806744.7, dated Feb. 22, 2018, 12 pages.
Chinese Office Action for Application No. 201580042846.4, dated Dec. 16, 2019, 10 pages.
Chinese Office Action on the Patentability of Application No. 201580042846.4, dated Nov. 3, 2020, 9 pages.
Chinese Office Action and Search Report for Application No. 201580042846.4, dated Jul. 20, 2020, 12 pages.
Extended European Search Report on the Patentability of Application No. 21159724.0 dated Jun. 15, 2021, 7 pages.

* cited by examiner

HANDHELD ULTRASOUND IMAGING SYSTEMS AND METHODS FOR COOLING TRANSDUCERS AND ELECTRONICS IN THE PROBE HOUSING VIA AIR CIRCULATION THROUGH THE HOUSING

TECHNICAL FIELD

The disclosed technology relates generally to ultrasound probes, and more specifically to systems and methods of reducing heat of ultrasound probes.

DETAILED DESCRIPTION

Figure 1A:
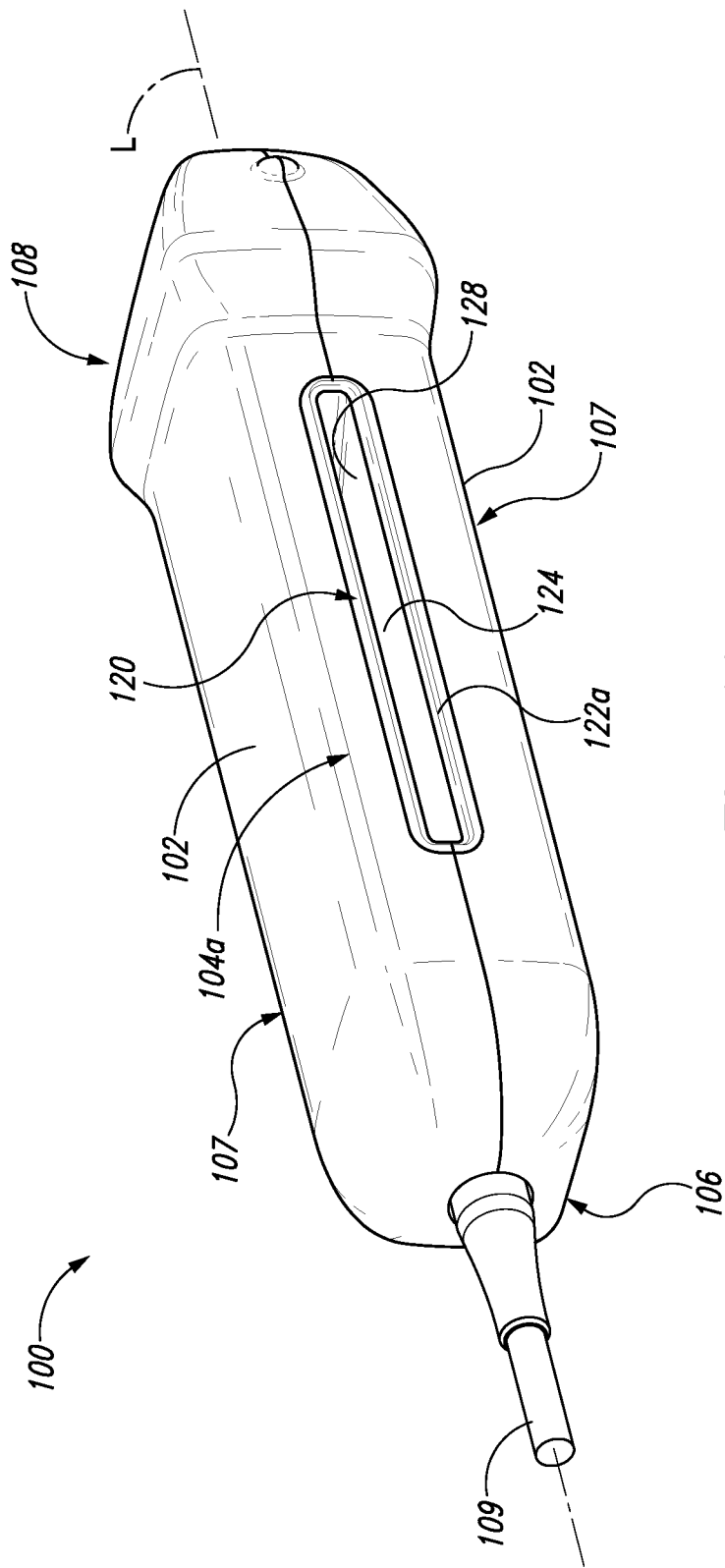
FIG. 1A is an isometric side view of an ultrasound transducer configured in accordance with the disclosed technology.

The disclosed technology is generally directed to systems and methods of cooling ultrasound transducers. It will be appreciated that several of the details set forth below are provided to describe the following embodiments in a manner sufficient to enable a person skilled in the relevant art to make and use the disclosed embodiments. Several of the details described below, however, may not be necessary to practice certain embodiments of the technology. Additionally, the technology can include other embodiments that are within the scope of the claims but are not described in detail with reference to FIGS. 1A-D.

The disclosed technology can reduce an amount of heat emitted from an outer surface of an ultrasound probe. During an ultrasound procedure, for example, an ultrasound transducer in the probe generates, transmits and receives ultrasound energy. Electronics in the probe (e.g., beamforming electronics) can process the signals and produce ultrasound data that can be used to form an ultrasound image. The generation of the ultrasound energy and processing of the ultrasound data can, in some instances, produce temperatures in excess of 60 degrees Celsius within the probe. Such temperatures may raise a temperature of at least a portion of the outer surface of the probe to a point of being uncomfortable or unsafe for an operator to hold and/or a patient to touch. Embodiments of the present technology include, for example, one or more conduits extending through an ultrasound probe allowing internal components to emit heat to air flowing through the conduit(s), thereby reducing a temperature along the outer surface of the probe and/or at the ultrasound transducer array.

In one embodiment, for example, a handheld ultrasound imaging probe includes a transducer assembly, electronics configured to drive the transducer and a housing surrounding the transducer assembly and the electronics. A heat spreader is positioned in the housing and configured to absorb heat from the transducer assembly and the electronics. A conduit extends from a slot in a first side of the housing to a slot in the second side of the housing and allows air to pass adjacent the heat spreader. In one aspect, the conduit has an interior surface sealed from an interior portion of the housing. One or both of the slots can be sized to prevent accessibility to the interior surface by a finger of an operator. For example, one of the slots can have a height that is significantly less than a width of the slot. In some aspects, the heat spreader can be bonded and/or integral to the conduit.

In another embodiment of the disclosed technology, a handheld ultrasound imaging probe includes a housing having a first side portion opposite a second side portion, and an ultrasound transducer array and a circuit disposed within the housing. A first aperture in the first side portion is in fluid communication with a second aperture in the second side portion via a conduit extending through the housing. The conduit includes a sealed interior surface that defines a cavity. In one aspect, the first and second apertures are sized to prevent accessibility by a finger of an operator to the cavity and the interior surface of the conduit. In another aspect, the ultrasound transducer includes a front end and a rear end, and the conduit includes a distal end and a proximal end. An exterior surface at the distal end of the conduit is shaped to define a recess that receives at least a portion of the ultrasound transducer. In some aspects, a thermally conductive material is disposed in the housing between an exterior surface of the conduit and the circuit. The thermally conductive material can have a higher thermal conductivity than the housing. In other aspects, the housing is configured to dissipate heat at a temperature less than or equal to a first temperature, and the interior surface of the conduit is configured to dissipate heat at a second temperature greater than the first temperature. In further embodiments, the interior surface of the conduit includes a plurality of grooves. In still further embodiments, the probe includes a second conduit through the housing that includes an interior surface that defines a second cavity. A third aperture is in fluid communication with a fourth conduit via the second cavity. The third and fourth apertures extend along different outer surfaces of the enclosure.

In yet another embodiment of the disclosed technology, a handheld imaging probe includes an ultrasound transducer array, beamforming electronics and an enclosure at least partially surrounding the transducer array and beamforming electronics. The enclosure includes a first opening and a second opening within different sides of the enclosure. The probe further includes a passive heat exchanger positioned in thermal communication with the transducer array and the beamforming electronics. The heat exchanger includes a sealed tube extending between the first and second openings, a heat spreader positioned at least proximate and/or near the tube, and an air passage defined by an inner surface of the tube. The tube is configured to convey thermal energy away from the ultrasound transducer, the beamforming electronics and the heat spreader via air flowing in and out of the tube through the air passage. In one aspect, the first and second openings are sized to inhibit accessibility of an operator's finger to the inner surface of the tube. In another aspect, the heat spreader has a higher thermal conductivity than the enclosure.

Figure 1B:
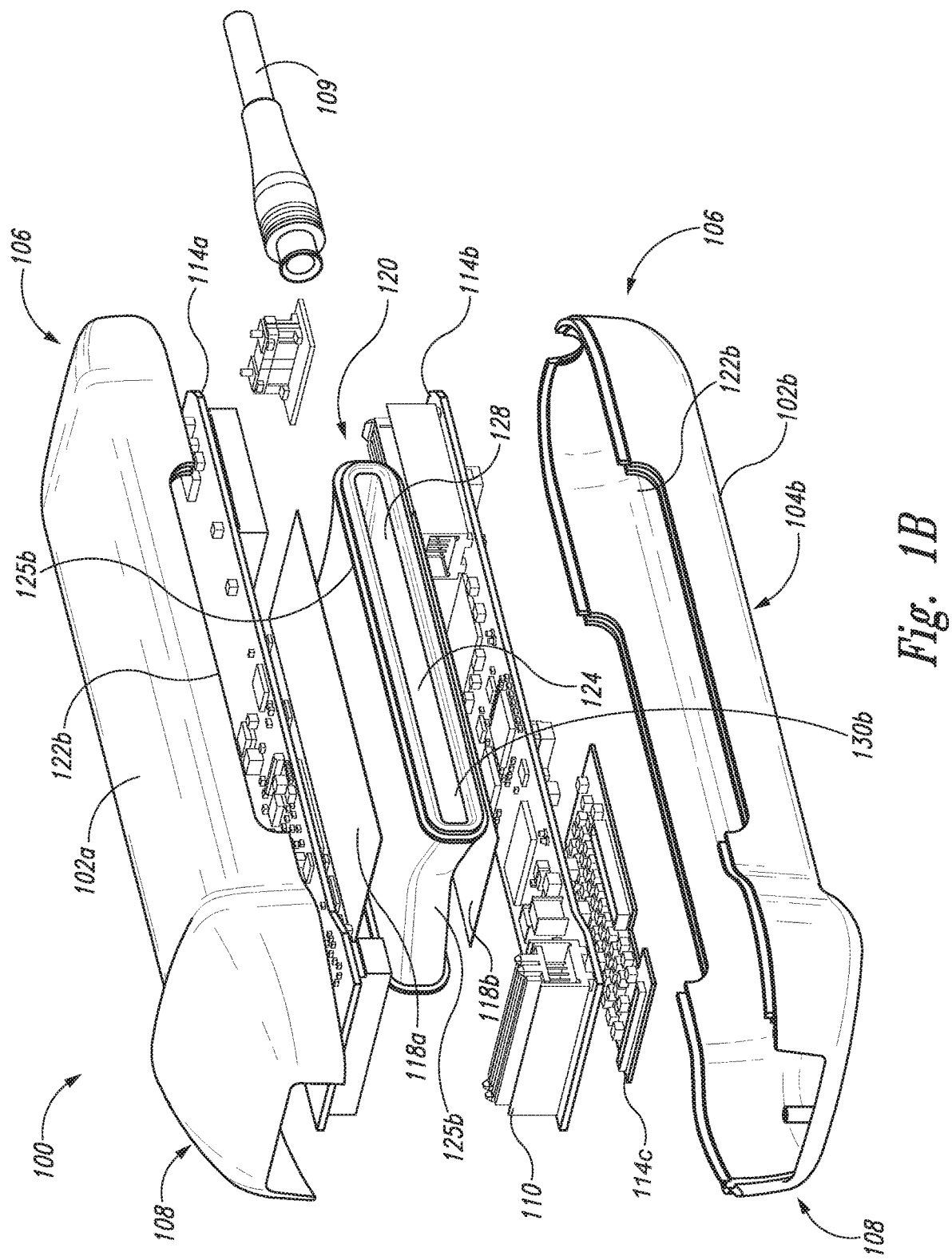
FIGS. 1B and 1C are isometric side exploded views of the ultrasound transducer of FIG. 1A.
Figure 1C:
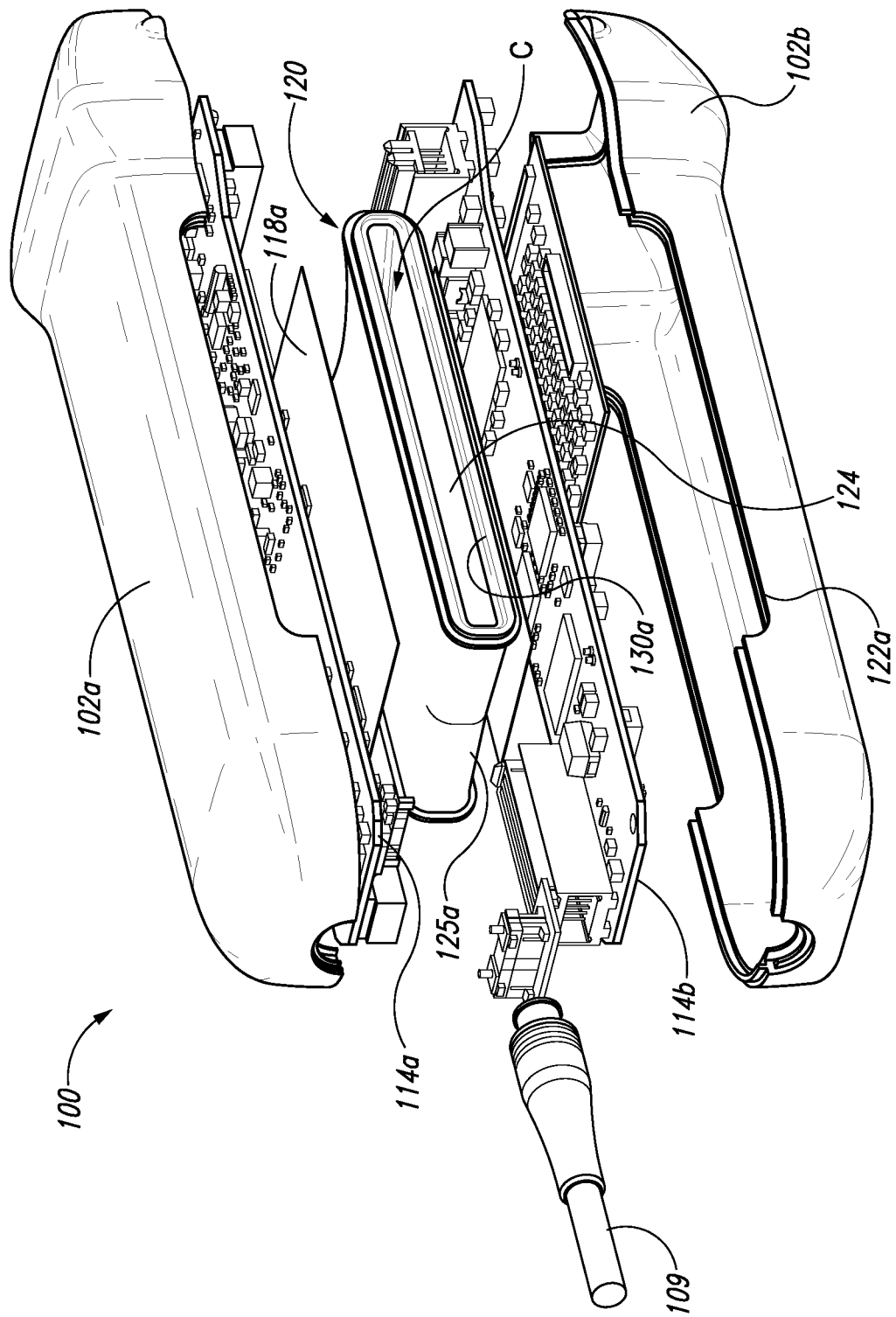
Figure 1D:
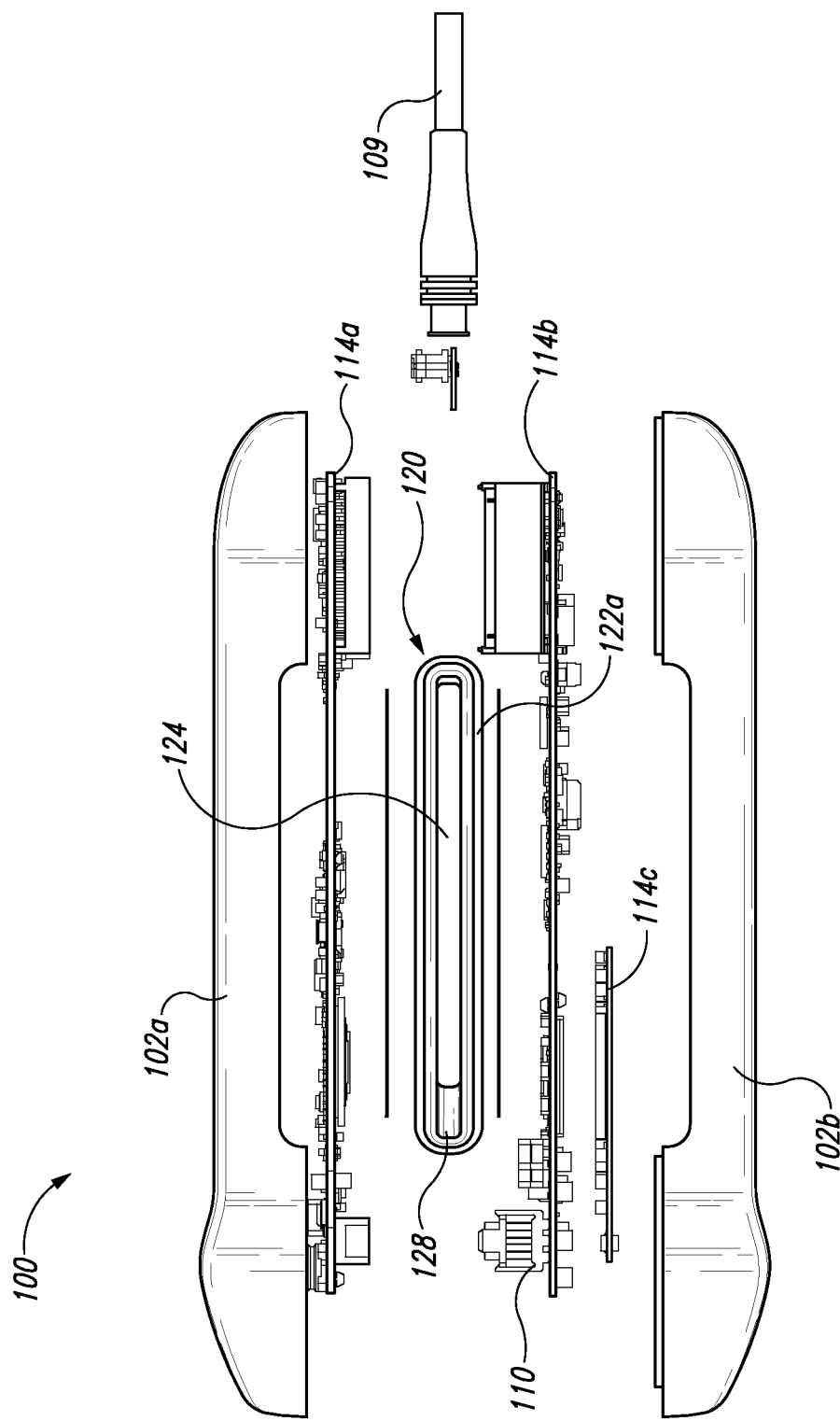
FIG. 1D is a side exploded view of the ultrasound transducer of FIG. 1A.

FIG. 1A is an isometric side view of an ultrasound transducer probe 100 configured in accordance with one embodiment of the disclosed technology. FIGS. 1B and 1C are exploded isometric side views of the probe 100. FIG. 1D is an exploded side view of the probe 100. Referring first to FIGS. 1A-1D together, the probe 100 includes a housing 102 (e.g., an enclosure, a body, a shell, etc.) that defines a cavity 103. The housing 102 includes a first housing portion 102a (e.g., an upper portion) attached or otherwise bonded to a second housing portion 102b (e.g., a lower portion). The housing 102 further includes a first side portion 104a and a second side portion 104b on opposite sides of a longitudinal axis L extending through a proximal end portion 106, an intermediate portion 107 and a distal end portion 108 of the housing 102. A first aperture 122a (e.g., an opening, a hole, etc.) forms an elongated slot that extends longitudinally along the first side portion 104a. A second aperture 122b (e.g., an opening, a hole, etc.) forms an elongated slot that extends longitudinally along the second side portion 104b. The first and second apertures 122a and 122b are configured to inhibit and/or block entry of a finger (e.g., an operator's finger, a patient's finger, etc.) therethrough. The first and second apertures 122a and 122b each have a length that extends between the proximal end portion 106 and the distal end portion 108 and a width that extends between the first housing portion 102a and the second housing portion 102b. In one embodiment, one or both of the length or the width of either the first aperture 122a or the second aperture 122b has a dimension less than a diameter of typical finger (e.g., less than about 5 mm). In some embodiments, for example, one or both of the first and second apertures 122a and 122b can include a length (e.g., between about 10 mm and about 100 mm, between about 15 mm and about 35 mm, or about 25 mm) significantly greater than a width (e.g., between about 2 mm and about 20 mm, between about 3 mm and about 5 mm, or about 4 mm). In further embodiments, a grid and/or a mesh screen, for example, can be disposed within one or both of the first and second apertures 122a and 122b to inhibit entry of a finger.

The housing 102 is configured to at least partially surround an ultrasound transducer assembly 110 (e.g., a single element ultrasound transducer, a one-dimensional ultrasound transducer array, a multi-dimensional ultrasound transducer array, etc.) positioned at least proximate the distal end portion 108. The transducer assembly 110 is electrically connected to system electronics 114 (identified separately as first system electronics 114a, second system electronics 114b and third system electronics 114c). The electronics 114 can include, for example, one or more digital signal processors, beamformers (e.g., analog and/or digital beamformers), image processors (e.g., one or more processors capable of processing B-mode images, M-mode images, Doppler images, etc.), electronic filters, etc. A cable 109 at the proximal end portion 106 communicatively couples the transducer assembly 110 and the system electronics 114 to an external computer and/or display (not/shown).

A conduit 120 (e.g., a duct, tube, etc.) extends through the housing 102 from the first aperture 122a toward the second aperture 122b. The conduit 120 includes a first conduit opening 130a (e.g., an inlet/outlet) and a second conduit opening 130b positioned adjacent the first aperture 122a and the second aperture 122b, respectively. The conduit 120 further includes a proximal end portion 125a opposite a distal end portion 125b. The distal end portion 125b includes an exterior surface defining a pocket or recess configured to receive at least a portion of the transducer assembly 110. In the illustrated embodiment, the conduit 120 is shown positioned in the intermediate portion 107 of the probe 100. In other embodiments, however, the conduit 120 can be positioned at any suitable location within the housing 102. Moreover, the probe 100 in FIGS. 1A-1D includes a single conduit 120. In other embodiments, however, the probe 100 can include a plurality of conduits 120 extending through the housing 102.

An interior surface 128 of the conduit 120 defines a fluid path 124 (e.g., an air pathway, air passage, cavity, through hole, etc.) between the first aperture 122a and the second aperture 122b. The interior surface 128 of the illustrated embodiment is sealed such that air within the conduit 120 cannot flow into the cavity 103. In some embodiments, however, the interior surface 128 can be at least partially open (e.g., via one or more holes or vents) to allow air in the fluid path 124 to flow in and out of the cavity 103. The interior surface 128 can be made from a material (e.g., copper, a copper alloy, aluminum, stainless steel, etc.) having a thermal conductivity greater than a material from which the housing 102 is formed. In other embodiments, however, the interior surface 128 can be made of any suitable heat-resistant material (e.g., thermally conductive materials capable of withstanding temperatures greater than 100 degrees Celsius). In further embodiments, the interior surface 128 can include one or more features (e.g., channels, grooves, ridges, notches, etc.) along at least a portion thereof to increase the surface area thereof, thereby increasing heat dissipation.

A first heat spreader 118a and a second heat spreader 118b are positioned adjacent the conduit 120 and in thermal communication with the interior surface 128, the transducer assembly 110, the electronics 114. The first and second heat spreaders 118a and 118b can comprise, for example, copper, an alloy of copper and/or any other suitable thermally conductive material (e.g., aluminum, graphite, composites that include aluminum and/or copper, etc.). The first and second heat spreaders 118a and 118b are configured to absorb heat from the transducer assembly 110 and in the electronics 114 and transmit heat to the interior surface 128. In some embodiments, for example, the first and second heat spreaders 118a and 118b are directly bonded to the conduit 120 and/or at least partially integrated into the conduit 120. In other embodiments, however, the heat spreaders 118a and 118b are fully integrated with the conduit 120.

The generation of ultrasound energy by the transducer assembly 110 during an ultrasound measurement procedure and/or the processing of ultrasound signals by the electronics 114 can produce significant amounts of heat. For example, during an ultrasound procedure, the transducer assembly 110 and electronics 114 may emit sufficient heat to raise a temperature at the interior surface 128 above for example, 60 degrees Celsius, which could be unsafe to touch. As explained above, however, first and second apertures 122a and 122b are configured to inhibit entry of a finger, thus reducing and/or blocking access to the interior surface 128 to an operator's and/or patient's touch. The disclosed technology therefore is expected to increase an amount of heat that can be produced and/or dissipated by the probe 100 compared to other ultrasound probes without the housing 102 being uncomfortable or unsafe to touch or hold.

In operation, a coolant C (e.g., air, water and/or another suitable coolant) can enter the conduit 120, flow through the fluid path 124 and absorb heat generated by components in the probe 100 before exiting the conduit 120. The coolant C, for example, can enter the conduit 120 at a first temperature through either of the first conduit opening 130a or the second conduit opening 130b. As the coolant C flows through the fluid path 124 in the conduit 120, the coolant C can absorb heat transmitted from, for example, the transducer assembly 110 and/or the electronics 114 via the heat spreaders 118a and 118b and the interior surface 128 thereby convectively cooling the probe 100 and one or more components contained therein.

From the foregoing, it will be appreciated that specific embodiments of the invention have been described herein for purposes of illustration, but that various modifications may be made without deviating from the scope of the invention. For example, although the conduit 120 between the first and second apertures 122a and 122b is shown as a single continuous opening, it will be appreciated that multiple conduits connecting multiple holes or slots can be provided along the length of the probe 100. Accordingly, the invention is not limited except as by the appended claims.

We claim:

1. A handheld ultrasound imaging probe, comprising:
   a transducer assembly provided at a distal end of the imaging probe;
   electronics configured to drive the transducer assembly, wherein the electronics are coupled to the transducer;
   a housing surrounding the transducer assembly and the electronics having a longitudinal axis extending between a proximal end of the imaging probe and the distal end of the imaging probe, wherein the housing includes a sealed conduit extending through the housing, wherein the sealed conduit includes a first aperture and a second aperture positioned on opposite sides of the housing, and wherein the conduit is aligned in a direction perpendicular to the longitudinal axis of the imaging probe;
   one or more heat spreaders within the housing configured to absorb heat from the transducer assembly and the electronics, wherein the one or more heat spreaders are located between the electronics and the sealed conduit of the imaging probe,
   wherein the electronics are located within the housing on two sides of the sealed conduit, wherein the sealed conduit is configured to dissipate heat by allowing air to flow through the sealed conduit, wherein an interior surface of the sealed conduit has a thermal conductivity that is greater than a thermal conductivity of the housing and is thermally coupled to the one or more heat spreaders to transfer heat from the transducer assembly and the electronics to the interior surface of the sealed conduit, wherein an exterior surface of the sealed conduit defines a sealed passageway through which air can pass from the first aperture to the second aperture and prevents the air from entering the housing, and wherein the sealed conduit is configured to remove the heat from the transducer assembly and the electronics by the air passing from the first aperture to the second aperture.

2. The probe of claim 1 wherein the first and second apertures are sized to prevent accessibility to the interior surface of the conduit by a finger of an operator.

3. The probe of claim 2 wherein the first and second apertures each of a length and a width, wherein the length is greater than or equal to 5 times the width.

4. The probe of claim 1 wherein the one or more heat spreaders are bonded to the conduit.

5. The probe of claim 1 wherein the one or more heat spreaders are integral to the conduit.

6. A handheld ultrasound imaging probe, comprising:
   a housing having a first side portion opposite a second side portion, and having a sealed conduit that defines a passageway through which air can pass, the sealed conduit extending from the first side portion to the second side portion and the sealed conduit include a first aperture in the first side portion and a second opening in the second side aperture;
   an ultrasound transducer assembly and circuits disposed within the housing, wherein the ultrasound transducer assembly is coupled to the circuits; and
   one or more heat spreaders thermally coupled to the ultrasound transducer assembly and the circuits, wherein the circuits are located within the housing on two sides of the sealed conduit, wherein the one or more heat spreaders are located between the circuits and the sealed conduit, wherein the sealed conduit is configured to dissipate heat by allowing air to flow through the sealed conduit, wherein an interior surface of the sealed conduit is made of a material having a higher thermal conductivity than the thermal conductivity of the housing and an exterior surface of the sealed conduit prevents air from entering the housing, wherein the sealed conduit is thermally coupled to the transducer assembly and to the circuits in the housing, to dissipate heat from the transducer assembly and the circuits by air passing through the passageway from one side portion of the housing to the opposite side portion of the housing.

7. The ultrasound probe of claim 6 wherein the the first and the second aperture are configured to prevent accessibility by a finger of an operator into an interior surface of the conduit.

8. The ultrasound probe of claim 6 wherein an exterior surface at a distal end of the conduit includes a recess that is configured to receive at least a portion of the ultrasound transducer.

9. The ultrasound probe of claim 6, further comprising a thermally conductive material disposed in the housing that is adjacent the conduit, wherein the thermally conductive material has a higher thermal conductivity than the housing.

10. A handheld imaging probe, comprising:
    an ultrasound transducer assembly and beamforming electronics coupled to the ultrasound transducer assembly;
    an enclosure surrounding the transducer assembly and the beamforming electronics, wherein the enclosure includes a first opening and a second opening within opposite sides of the enclosure;
    a sealed conduit positioned in thermal communication with the transducer array and the beamforming electronics, wherein the
    sealed conduit extends from the first opening to the second opening, wherein an interior surface of the sealed conduit is made of a material having a higher thermal conductivity than a thermal conductivity of the enclosure that allows air to pass from the first opening to the second opening and an external surface of the sealed conduit prevents air from entering the enclosure, wherein the beamforming electronics are located within the enclosure on two sides of the conduit, wherein the conduit is configured to dissipate heat by allowing air to flow through the conduit; and
    one or more heat spreaders thermally coupled to the transducer array and the beamforming electronics and to the conduit so that heat from the transducer array and the beamforming electronics is dissipated by air passing through the sealed conduit from the first opening to the second opening, wherein the one or more heat spreaders are located between the beamforming electronics and the sealed conduit.

11. The imaging probe of claim 10 wherein the first and second openings each have a length and a width, wherein the length is greater than or equal to 5 times the width.

* * * * *